United States Patent [19]

Noda

[11] Patent Number: 5,918,747

[45] Date of Patent: Jul. 6, 1999

[54] PROCESS FOR RECOVERING POLYHYDROXYALKANOATES USING CENTRIFUGAL FRACTIONATION

[75] Inventor: Isao Noda, Fairfield, Ohio

[73] Assignee: The Procter & Gamble Company, Cincinnati, Ohio

[21] Appl. No.: 08/910,869

[22] Filed: Jul. 13, 1997

Related U.S. Application Data

[63] Continuation of application No. 08/251,828, Jun. 1, 1994, abandoned.
[51] Int. Cl.$^6$ .............................. B03B 5/30; B03B 5/32; B03B 5/34
[52] U.S. Cl. ...................... 209/155; 209/725; 435/136; 435/142; 528/502 R; 528/502 D
[58] Field of Search .......................... 209/10, 155, 725; 435/146, 136, 142; 528/502 R, 502 D

[56] References Cited

U.S. PATENT DOCUMENTS

| | | | |
|---|---|---|---|
| 3,036,959 | 5/1962 | Baptist et al. | 435/146 |
| 3,828,017 | 8/1974 | Finley et al. | |
| 3,869,438 | 3/1975 | Finley et al. | |
| 3,895,003 | 7/1975 | Swain et al. | |
| 4,146,534 | 3/1979 | Armstrong . | |
| 4,154,623 | 5/1979 | Schwengers et al. | 127/39 |
| 4,174,314 | 11/1979 | Garrison . | |
| 4,174,315 | 11/1979 | Garrison et al. | |
| 4,175,075 | 11/1979 | Garrison et al. | |
| 4,215,040 | 7/1980 | Hager . | |
| 5,334,520 | 8/1994 | Dennis | 435/136 |

FOREIGN PATENT DOCUMENTS

| | | |
|---|---|---|
| 0 015 123 | 9/1980 | European Pat. Off. . |
| 0 046 335 | 2/1982 | European Pat. Off. . |
| 91/00917 | 1/1991 | WIPO . |
| 91/13207 | 9/1991 | WIPO . |
| 92/19747 | 11/1992 | WIPO . |

OTHER PUBLICATIONS

"Novel Biodegradable Microbial Polymers", E.A. Dawes, Ed., NATO ASI Series, Series E:Applied Sciences, vol. 186 (1990; no month cited).

Peoples, O.P. and A.J. Sinskey, "Poly–β–hydroxybutyrate (PHB) Biosynthesis in *Alcaligenes eutrophus* H16", The Journal of Biological Chemistry, vol. 264, No. 26, pp. 15298–15303 (Sep. 1989).

Poirier, Y., D. Dennis, K. Klomparens, C.Nawarath and C. Somerville, "Perspectives on the Production of Polyhydroxyalkanoates in Plants", FEMS Microbiology Reviews, vol. 103, pp. 237–246 (1992; no month cited).

Poirier, Y., D.E. Dennis, K. Klomparens and C. Somerville, "Polyhydroxybutyrate, a Biodegradable Thermoplastic, Produced in Transgenic Plants", Science, vol. 256, pp. 520–523 (Apr. 1992).

Doi, Y., "Microbial Synthesis, Physical Properties and Biodegradability of Polyhydroxyalkanoates", Advances in Biopolymer Engineering Conference, (Jan. 23–28, 1994).

Poole, R., In Search of the Plastic Potato, Science, vol. 245, pp. 1187–1189 (Sep. 1989).

Smith, E., K.A. White, D. Holt, P.A. Fentem, and S.W.J. Bright, "Expression of Polyhydroxybutyrate in Oilseed Rape", Advances in Biopolymer Engineering Conference, (Jan. 23–28, 1994).

Fukui et al. "Enzymatic Synthesis of Poly–B–Hydroxy–butyrate in Zoogloea ramiger", Archives of Microbiology, 110, pp. 149–156 (Nov. 1976).

Concise Encyclopedia of Chemistry, 1993, pp. 507–508, Dr. Hans–Dieter Jakabe and Dr. Hans Jeschkeit, eds.

Nickerson "Purification of Poly–B–Hydroxybutyrate . . . " Applied and Environmental Microbiology, May 1982, pp. 1208–1209.

Concise Encyclopedia of Chemistry, Walter de Gruyter & Co., Berlin, English Language ed. (1993), pp. 507–508.

Lundgren et al. "Structure of Poly–B–hydroxybutyric Acid Granules", J. gen. Microbiol. (1964), 34, 441–446.

Merrick et al., "Depolymerization of Poly–B–hydroxy–butyrate by an Intra cellular Enzyme System", Journal of Bacteriology, vol. 88, No. 1, pp. 60–71 (1964).

*Primary Examiner*—Jeffrey C. Mullis
*Attorney, Agent, or Firm*—Brahm J. Corstanje; Bart S. Hersko; David L. Suter

[57] ABSTRACT

The present invention relates to a process for recovering polyhydroxyalkanoate from a biological source material containing the polyhydroxyalkanoate, the process comprising: a) comminuting the biological source material; b) suspending the comminuted biological source material in a fluid; c) partitioning the polyhydroxyalkanoate from the other components of the biological source material by centrifugal fractionation to form a solid-solid separation; and d) recovering the polyhdroxyalkanoate.

11 Claims, No Drawings

PROCESS FOR RECOVERING POLYHYDROXYALKANOATES USING CENTRIFUGAL FRACTIONATION

This is a continuation of application Ser. No. 08/251,828, filed on Jun. 1, 1994 now abandoned.

TECHNICAL FIELD

The present invention relates to processes for isolating specific resin components from other biomass components. More specifically, the present invention relates to a process for the recovery of a polyhydroxyalkanoate from a biological system, such as a plant or bacteria, by using centrifugal fractionation.

BACKGROUND

Commodity polymers are typically produced from petrochemical sources by well-known synthetic means. However, recent advances in technology have resulted in the promise of new sources of commodity polymers. Particularly promising is the production of plastic resins using living organisms ("bioplastic"), including genetically manipulated bacteria and crop plants, which are designed to produce polymers such as polyhydroxyalkanoate (PHA); a number of bacteria which naturally produce PHA are also promising sources of PHA. (see for example, NOVEL BIODEGRADABLE MICROBIAL POLYMERS, E. A. Dawes, ed., NATO ASI Series, Series E: Applied Sciences—Vol. 186, Kluwer Academic Publishers (1990); Poirier, Y., D. E. Dennis, K. Klomparens and C. Somerville, "Polyhydroxybutyrate, a biodegradable thermoplastic, produced in transgenic plants", SCIENCE, Vol. 256, pp. 520–523 (1992)). In a large scale production, for example agricultural production, the harvesting and purifying of such bioplastic from the biomass debris is a critical step for determining the practical feasibility of such technology.

The separation of polymeric lipids such as PHA from a large-scale biological source, such as an agricultural crop, is not a trivial task. The conventional separation methods used extensively in the extraction of low molecular weight lipids are not practical to employ in a resin isolation process. For example, a simple mechanical press is impractical because, unlike separating vegetable oils from oil-seeds, solid plastics cannot be squeezed out of crops by mechanical pressing.

Solvent extraction is also impractical for a number of reasons. A solution of polymer develops an extremely high viscosity, even at relatively low concentration, thereby making the solution extremely difficult to work with. Furthermore, the stripping of solvent from polymer is a slow and difficult process. A commonly used solvent for the extraction of PHA from bacteria is chloroform. However, the use of a large amount of such a solvent, potentially harmful to health and environment if accidentally released, near the harvesting site would be undesirable.

Separation of PHA by sedimentational methods should be, in principle, possible. However, simple gravitational (1-G force) settling in a liquid suspending medium is, in fact, quite impractical. The rate of settling is extremely slow. In addition, such slow settling is easily disrupted by the Brownian motion of the fine PHA particles induced by the thermal fluctuation of the suspending fluid molecules surrounding the particles. Furthermore, the extended period of time required to settle very fine PHA particles introduces the problem of bacterial contamination and subsequent biodegradation of the particle suspension.

Based on the foregoing, there is a need for a simple and economical process for recovering bioplastics from a large-scale biological source. Such a process would preferably be easily adaptable as an integral part of the agricultural production of bioplastics.

It is therefore an object of the present invention to provide a process for recovering bioplastics from a biological source material.

SUMMARY

The present invention relates to a process for recovering polyhydroxyalkanoate from a biological source material containing the polyhydroxyalkanoate, the process comprising: a) comminuting the biological source material; b) suspending the comminuted biological source material in a fluid; c) partitioning the polyhydroxyalkanoate from the other components of the biological source material by centrifugal fractionation to form a solid-solid separation; and d) recovering the polyhdroxyalkanoate.

DETAILED DESCRIPTION

The present invention answers the need for a process for recovering bioplastics from a biological source material.

The following is a list of definitions for terms used herein.

"g/sec" means grams per second.

"g/min" means grams per minute.

"$\mu$" means micron(s).

"psi" means pounds per square inch.

"MPa" means mega pascal, which is equivalent to about 145 psi.

"Fractionation" means the separation and/or isolation of components of a mixture. The invention described herein preferably achieves such fractionation due to differences in the density and/or particle size of the various components.

"Solid-solid separation" and "solid-solid fractionation" mean the separation or partitioning of components in a sample wherein each fraction comprises a component in a solid state. For example, a separation resulting in a fraction comprising PHA granules suspended in a fluid medium and a fraction comprising other insoluble biomass is considered a solid-solid separation.

"Liquid-solid separation" and "liquid-solid fractionation" mean the separation or partitioning of components in a sample wherein at least one fraction contains an otherwise solid component in liquid state, and at least one fraction comprises a component in a solid state. For example, a separation resulting in a fraction comprising PHA dissolved in a solvent and a fraction comprising other insoluble biomass is considered a liquid-solid separation.

"Polyhydroxyalkanoate" and "PHA" mean a polymer having the following general structure:

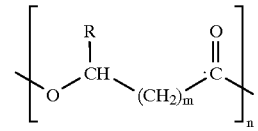

wherein R is preferably an alkyl or alkenyl, m is 1 or 2, and n is an integer. The structure enclosed in brackets is commonly referred to as a repeating unit. The terms polyhydroxyalkanoate and PHA include polymers containing one or more different repeating units. Examples of preferred PHAs recoverable by the present process included those disclosed in U.S. Pat. No. 5,489,470, Noda, issued Feb. 6, 1996; World Patent Application 95/20621, Noda, published Aug. 3, 1995; World Patent Application 95/20615, Noda, published Aug. 3, 1995; and U.S. Pat. No. 5,292,860, Shiotani and Kobayashi, issued Mar. 8,1994.

"Recovering polyhydroxyalkanoate from a biological source material", in addition to referring to the recovery of the particular PHA produced by a biological source material which produces a single PHA, also refers to the recovery of one or more types of PHA when the biological source material produces more than one type of PHA.

"Alkyl" means a carbon-containing chain which may be straight, branched or cyclic, preferably straight; substituted (mono- or poly-) or unsubstituted; and saturated.

"Alkenyl" means a carbon-containing chain which may be straight, branched or cyclic, preferably straight; substituted (mono- or poly-) or unsubstituted; and monounsaturated (i.e., one double or triple bond in the chain), or polyunsaturated (i.e., two or more double bonds in the chain, two or more triple bonds in the chain, or one or more double and one or more triple bonds in the chain).

"Comprising" means that other steps and other ingredients which do not affect the end result can be added. This term encompasses the terms "consisting of" and "consisting essentially of".

All percentages are by weight of total composition unless specifically stated otherwise.

The present invention relates to a process for recovering (i.e., isolating) polyhydroxyalkanoate from a biological source material containing the polyhydroxyalkanoate, the process comprising centrifugal fractionation of the biological source material such that the polyhydroxyalkanoate is partitioned from the other components of the biological source material by solid-solid separation.

PHA components found in biological systems (e.g., conventional, or genetically engineered bacteria or genetically engineered plants) tend to settle at rates different from other cellular components such as proteins and carbohydrates when they are suspended in a common fluid medium. The difference in the sedimentation rate results in the spatial segregation of mixed particulates into multiple layers (fractionation) each containing predominantly a single component.

According to the Stokes'law of sedimentation, there are two major factors affecting the sedimentation rates of particles: differences in the density and size of suspended particles. These factors independently control the separation efficiency of the fractionation process.

Density is an intrinsic property of the material to be separated. Generally, there is no easy way of manipulating the density of an individual component to be fractionated. The density difference between particles in a composition is not always large enough to achieve substantial fractionation of one component from the rest. When the densities of the components are sufficiently different, a high degree of separation can be achieved, particularly when a suspending medium having an intermediate density is used. The density of PHA is sufficiently different from other biomass components, such as proteins and carbohydrates, to achieve some degree of fractionation.

Differences in particle size also contribute greatly to the effectiveness of the fractionation process. PHA is generally stored in biological systems in the form of very fine granules having a diameter of about or below $1\mu$. The particle size of PHA granules are therefore much smaller as compared to other cellular components from the disrupted cell. In addition, particle size can be further manipulated by a post-harvest processing which includes grinding or colloid-milling. Specific types of biological source material and the process are discussed in more detail below.

Biological Source Material

Sources from which PHA is recovered via the process of the present invention include single-cell organisms such as bacteria or fungi and higher organisms such as plants (herein collectively referred to as "biological source material" or "BSM"). While such BSM could be wild-type organisms, they are preferably genetically manipulated species specifically designed for the production of a specific PHA of interest to the grower. Such genetically manipulated organisms are produced by incorporating the genetic information necessary to produce PHA. Typically, such genetic information is derived from bacteria which naturally produce PHA.

Plants useful in the present invention include any genetically engineered plant designed to produce PHA. Preferred plants include agricultural crops such cereal grains, oil seeds and tuber plants; more preferably, avocado, barley, beets, broad bean, buckwheat, carrot, coconut, copra, corn (maize), cottonseed, gourd, lentils, lima bean, millet, mung bean, oat, oilpalm, peas, peanut, potato, pumpkin, rapeseed (e.g., canola), rice, sorghum, soybean, sugarbeet, sugar cane, sunflower, sweetpotato, tobacco, wheat, and yam. Such genetically altered fruit-bearing plants useful in the process of the present invention include, but are not limited to apple, apricot, banana, cantaloupe, cherries, grapes, kumquat, lemon, lime, orange, papaya, peaches, pear, pineapple, tangerines, tomato, and watermelon. Preferably the plants are genetically engineered to produced PHA pursuant to the methods disclosed in Poirier, Y., D. E. Dennis, K. Klomparens and C. Somerville, "Polyhydroxybutyrate, a biodegradable thermoplastic, produced in transgenic plants", SCIENCE, Vol. 256, pp. 520–523 (1992), World Pat. Application 95/05472, Somerville, Nawrath and Poirier, published Feb. 23, 1995; and World Pat. Application 93/02187, Somerville, Poirier and Dennis, published Feb. 4,1993. U.S. Pat. No. 5,650,555, Dennis et al., issued Jul. 22, 1997, and U.S. Pat. No. 5,610,041, Nawrath et al., issued Mar. 11, 1997. Particularly preferred plants are soybean, potato, corn and coconut plants genetically engineered to produce PHA.

Bacteria useful in the present invention include any genetically engineered bacteria designed to produce PHA, as well as bacteria which naturally produce PHA. Examples of such bacteria include those disclosed in NOVEL BIODEGRADABLE MICROBIAL POLYMERS, E. A. Dawes, ed., NATO ASI Series, Series E: Applied Sciences—Vol. 186, Kluwer Academic Publishers (1990); U.S. Pat. No. 5,250,430, Peoples and Sinskey, issued Oct. 5, 1993; U.S. Pat. No. 5,245,023, Peoples and Sinskey, issued Sep. 14, 1993; U.S. Pat. No. 5,229,279, Peoples and Sinskey, issued Jul. 20, 1993; and U.S. Pat. No. 5,149,644, Lubitz, issued Sep. 22, 1992.

It is preferable that the BSM contain a sufficient quantity of PHA to make the process economically desirable. Preferably, the initial content of PHA in the source material should be at least about 5% of the total dry weight; more preferably at least about 25%; more preferably at least about 50%; more preferably still, at least about 75%.

Isolation Process

The process of the present invention preferably involves the following unit-operation steps: pretreatment, size reduction, suspension, and centrifugal separation. The optimal range of unit operation conditions or individual devices will vary considerably according to the type of raw BSMs used.

The pretreatment of source materials comprising PHA is preferred in order to remove low molecular weight contaminants readily soluble in appropriate solvents, such as sugars, oils and sometimes moisture. A variety of standard pretreatment methods used for the processing of food crops are known to those skilled in the art and may be readily employed for the pretreatment step of the present invention. Examples of such pretreatment steps include oil extraction (for example, see BAILEY'S INDUSTRIAL OIL AND FAT PRODUCTS, THIRD ED., Johne Wiley and Sons: New York (1964), pp. 663–713), water washing (for example, see U.S. Pat. No. 2,881,076, Sair, issued Apr. 7, 1959), and alcohol washing (for example, see Eldridge, A. C., W. J. Wolf, A. M. Nash and A. K. Smith, "Alcohol Washing of Soybean Protein", AGRICULTURAL AND FOOD CHEMISTRY, July–August, 1963, pp. 323–328).

The pretreated material comprising PHA granules is then pulverized (e.g., dry milling) to small fragments, by first using, for example a common vibratory or hammer mill. The pulverization of source material by dry milling, particularly for agricultural crop plants comprising PHA granules, preferably produces grain flour of a particle size finer than about $500\mu$ in diameter, more preferably finer than about $300\mu$, more preferably still, finer than about $100\mu$.

The comminuted material is then dispersed in a suspending fluid such as water, chlorinated carbon solvents (e.g., chloroform, carbon tetrachloride, or dichlorethane), various organic solvents (e.g., ethanol, methanol, acetone, methyl ethyl ketone, ethyl acetate, hexane, heptane, pentane, or mixtures thereof), or supercritical fluids (e.g., carbon dioxide or nitrous oxide); preferably water. If the suspending fluid is water, the water is preferably heated to promote hydration of certain non-PHA components prior to the wet milling to a temperature preferably not exceeding 90° C. If a suspending medium having an intermediate density between the PHA and other biomass is desired, then the suspending medium is preferably an aqueous solution of an organic or inorganic salt, or an aqueous solution of a water-soluble sugar. Useful organic salts include, but are not limited to, potassium glycolate, potassium citrate, potassium lactate, potassium malate, and dipotassium tartrate. Useful inorganic salts include, but are not limited to, sodium chloride, potassium chloride, calcium chloride, magnesium chloride, and calcium sulfate. Useful water-soluble sugars include, but are not limited to, sucrose, glucose, and raffinose.

The material is further treated by wet milling using a device such as a colloid mill, sonicator, or homoginizer, to obtain the desired particle size distribution for the dispersed solids. For wet milling, the comminuted material is suspended in a fluid. Preferred fluids include, but are not limited to water; ethanol; and aqueous solutions of organic salts, inorganic salts or sugars. The wet milling should preferably produce suspensions having an average particle size of smaller than about $50\mu$.

The suspension mixture of PHA and other biomass components is then processed with a centrifugal device to fractionate PHA-rich particles from the other biomass. Preferred centrifugal devices include, but are not limited to, centrifuge, ultracentrifuge, or hydrocyclone separator. An industrial scale centrifugal separation device may be used in the process of the present invention for fractionation of the PHA, so long as the device provides sufficient "G" force (i.e., sedimentational force field created, for example, by centrifugal effect expressed in terms of the equivalent to gravitational force) to achieve the sedimentation of solid particles above the rate necessary to overcome the Brownian motion of particles to be settled. The centrifugal force field employed in the process of the present invention is preferably at least about 10 G (i.e., ten times faster than simple gravimetric settling) to achieve rapid and efficient fractionation of PHA from other biomass components. More preferably, the centrifugal force field is at least about 100 G, more preferably at least about 1,000 G. more preferably at least about 10,000 G, more preferably still at least about 100,000 G.

In one embodiment of the present invention, a hydrocyclone is employed as the centrifugal device. A hydrocyclone consists of a conical cavity with an eccentric inlet port and two exit ports above and below the conical cavity. The vortex flow created by the off-centered high-speed injection of fluid creates a centrifugal force resulting in the sedimentation of heavy particles toward the inner wall of the conical cavity. The heavier portion will exit predominantly from the smaller tip of the cone, while the lighter portion will exit from the wider part of the cone. The centrifugal force field increases in a hydrocyclone with the inlet feed rate and decreases with the diameter of the conical cavity. For example, in a typical 1 cm diameter hydrocyclone, it is possible to achieve well above 100 G of centrifugal force by maintaining the feed rate of suspension above several tens of gallons per minute. (See, for example, Day, R. W., "Hydrocyclones in Process and Pollution Control", CHEMICAL ENGINEERING PROGRESS, Vol. 69, pp. 67–72 (1973); and U.S. Pat. No. 2,754,968, Vegter and Hage, issued Jul. 17, 1956; and KIRK-OTHMER ENCYCLOPEDIA OF CHEMICAL TECHNOLOGY, THIRD ED., Vol. 12, pp. 1–29, John Wiley and Sons, (1990)). Hydrocyclones useful in the present invention are available from a variety of manufactureres including Dorr-Oliver, Inc. (Milford, Conn.), Yardney Water Management Systems, Inc. (Riverside, Calif.), and Quality Solids Separation Co. (Houston, Tex.).

In another embodiment of the present invention, a continuous centrifuge may be employed as the centrifugal device. A continuous centrifuge comprises a rapidly rotating cylinder having a feed suspension flowing inside the cylinder. As a result of the rotation, centrifugal force is created thereby promoting sedimentation of heavier components toward the inner wall of the rotating cylinder. The sedimentate is continuously collected by a scraping mechanism while the supernatant is removed as effluent. A typical industrial scale centrifuge operating at several thousand rpm can easily produce a centrifugal force well above 100 G. (See, for example, Ambler, C. M., "The Evaluation of Centrifuge Performance", CHEMICAL ENGINEERING PROGRESS, Vol. 48, pp. 150–158, (1952); and KIRK-OTHMER ENCYCLOPEDIA OF CHEMICAL TECHNOLOGY, THIRD ED., Vol. 12, pp. 1–29 John Wiley and Sons, (1990)). Centrifuges useful in the present invention are available from a variety of manufacturers, including Humboldt Decanter, Inc. (Atlanta, Ga.), Western States Machine Co. (Hamilton, Ohio), and Bird Machine Co. (South Walpole, Mass.).

Preferably, the process of the present invention yields at least about 70% of the PHA in the source material, more preferably at least about 80%, more preferably still at least about 90%.

Preferably, at least about 85% of the dry mass of the PHA-rich fraction isolated by the process of the present invention is PHA, more preferably at least about 95%, more preferably still at least about 99%.

The PHAs recovered by the process of this invention are useful for forming a variety of plastic articles, including those disclosed in U.S. patent application Ser. No. 08/187, 969, Noda, filed Jan. 28, 1994; U.S. Pat. No. 5,489,470, Noda, issued Feb. 6, 1996; World Patent Application 95/20621, Noda, published Aug. 3, 1995; World Patent Application 95/20615, Noda, published Aug. 3, 1995. Such plastic articles include, but are not limited to, films, sheets, foams, fibers, nonwovens, elastomers, adhesive and molded articles. Such plastic articles can be further incorporated into a variey of useful products including, but not limited to, personal cleansing wipes; disposable health care products such as bandages, wound dressings, wound cleansing pads, surgical gowns, surgical covers, surgical pads; other institutional and health care disposables such as gowns, wipes, pads, bedding items such as sheets and pillowcases, foam mattress pads.

The following non-limiting examples illustrate the methods of the present invention.

EXAMPLE 1

Isolation of Poly(3-hydroxybutyrate-co-3-hydroxyoctanoate) from Soybeans

Soybeans, from a genetically altered soybean plant, comprising poly(3-hydroxybutyrate-co-hydroxyoctanoate) are roll milled to form thin flakes. The low molecular weight lipids and oils contained in the flakes are initially removed by pressing the flakes. The remaining low molecular lipids and oils are subsequently extracted from the flakes by using hexane as a solvent. The resulting defatted soybean flakes are dried and pulverized using a vibratory energy mill (Sweco, Florence, Ky.) to produce a flour having an average particle size of less than $80\mu$. The flour is then hydrated in water at 65° C. for 30 minutes to produce a suspension containing 7% solids by weight. The suspension is then passed through a colloid mill (Littleford Day, Florence, Ky.) once to assure complete mixing. The suspension is then passed through a homogenizer (Model 3M, APV Gaulin, Willimington, Mass.) operated at 8,000 psi, two times, to produce a suspension mixture consisting of fine granules of polymer having an average particle size of less than $1\mu$ and other soybean biomass debris comprising proteins and carbohydrates. The homogenized suspension of soybeans is fed to a hydrocyclone (DOXIE TYPE-A, Dorr-Oliver, Milford, Conn.) with a heavy duty pump (Model 4678-10S, Northern Pump, Minneapolis, Minn.) at a feed rate of 150 g/sec under a nominal pressure of 3 MPa. The effluent stream coming out the top section of the hydrocyclone contains most of the polymer granules. This portion of the suspension is spray dried and washed with 40% water/60% ethanol mixture to remove soluble residual components such as sugars, to produce a cake of poly(3-hydroxybutyrate-co-hydroxyoctanoate) granules with a purity of greater than 95%, and a yield of about 85% with respect to the starting material.

EXAMPLE 2

Isolation of Poly(3-hydroxybutyrate-co-hydroxyhexanoate) from Maize

Grains of maize (corn), from a genetically altered maize plant, comprising poly(3-hydroxybutyrate-co-3-hydroxyhexanoate are hammer milled to form meals. The low molecular weight lipids and oils contained in the meals are removed first by pressing the flakes and are then further extracted by using hexane as the solvent and washed with 40% water/60% ethanol mixture to remove other soluble components such as sugars. The resulting defatted and desugared maize meals are dried and comminuted using a vibratory energy mill (Sweco, Florence, Ky.) to produce a flour having an average particle size of less than $80\mu$. The flour is then hydrated in water at 65° C. for 30 min to produce a suspension containing 7% solids by weight. The suspension is then passed through a colloid mill (Littleford Day, Florence, Ky.) once to assure complete mixing. The suspension is then passed twice through a homogenizer (Model 3M, Gaulin, Willmington, Mass.) operated at 8,000 psi to produce a suspension mixture consisting of fine granules of poly(3-hydroxybutyrate-co-3-hydroxyhexanoate having an average particle size of less than $1\mu$ and other maize biomass debris comprising proteins and carbohydrates. The homogenized suspension of soybeans is fed to a continuous centrifuge (6" Solid Bowl Centrifuge, Bird Machine Co., South Walpole, Mass.) at a feed rate of 1,500 g/min. The supernatant effluent stream coming out the continuous centrifuge is spray dried to produce a cake of poly(3-hydroxybutyrate-co-3-hydroxyhexanoate granules with a purity higher than 98%, and a yield of about 85% with respect to the starting material.

EXAMPLE 3

Isolation of Poly(3-hydroxybutyrate-3-hydroxyvalerate) from Tobacco

Tobacco leaves, from a genetically altered tobacco plant, comprising poly(3-hydroxybutyrate-co-3-hydroxyvalerate) are hammer milled to form a flour. The low molecular weight soluble components contained in the flakes are removed by washing first with hexane and then with a 40% water/60% ethanol mixture to produce a dry flour having an average particle size of less than $80\mu$. The flour is then hydrated in water at 65° C. for 30 min to produce a suspension containing 7% solids by weight. The suspension is then passed through a colloid mill (Littleford Day, Florence, Ky.) once to assure complete mixing. The suspension is then passed twice through a homogenizer (Model 3M, Gaulin, Wilmington, Mass.) operated at 8,000 psi to produce a suspension mixture consisting of fine granules of poly(3-hydroxybutyrate-co-3-hydroxyvalerate) having an average particle size of less than $1\mu$ and other tobacco biomass debris. The homogenized suspension of tobacco is fed to a continuous centrifuge (6" Solid Bowl Centrifuge, Bird Machine Co., South Walpole, Mass.) at a feed rate of 1,500 g/min. The supernatant effluent stream coming out the continuous centrifuge is spray dried to produce a cake of poly(3-hydroxybutyrate-co-3-hydroxyvalerate) granules with a purity higher than 95%, and a yield of about 85% with respect to the starting material.

EXAMPLE 4

Isolation of Poly(3-hydroxybutyrate-co-3-hydroxydecanoate) from Coconuts

Coconuts, from a genetically altered coconut tree, comprising poly(3-hydroxybutyrate-co-3-hydroxydecanoate) are shredded to form thin flakes. The low molecular weight lipids and oils contained in the flakes are extracted by using hexane as a solvent. Soluble sugars are also removed by using a 40% water/60% ethanol mixture. The resulting defatted and desugared coconut flakes are dried and pulverized using a vibratory energy mill (Sweco, Florence, Ky.) to produce a flour having an average particle size of less than $80\mu$. The flour is then hydrated in water at 65° C. for 30 min to produce a suspension containing 7% solids by weight. The suspension is then passed through a colloid mill (Littleford Day, Florence, Ky.) once to assure complete mixing. The suspension is then passed twice through a homogenizer (Model 3M, Gaulin, Wilmington, Mass.) operated at 8,000 psi to produce a suspension mixture consisting of fine granules of poly(3-hydroxybutyrate-co-3-hydroxydecanoate) having an average particle size of less than 1μ and other coconut biomass debris. The homogenized suspension of coconuts is fed to a hydrocyclone (Doxie Type-A, Dorr-Oliver, Milford, Conn.) with a heavy duty pump (Model 4678-10S, Northern Pump, Minneapolis, Minn.) at a feed rate of 200 g/sec under a nominal pressure of 4 MPa. The effluent stream coming out the top section of the hydrocyclone will contain most of the poly(3-hydroxybutyrate-co-3-hydroxydecanoate) granules. This portion of the suspension is spray dried to produce a cake of poly(3-hydroxybutyrate-co-3-hydroxydecanoate) granules with a purity higher than 95%, and a yield of about 85% with respect to the starting material.

EXAMPLE 5

Isolation of Poly(3-hydroxybutyrate-co-3-hydroxyheptanoate) from Potatoes

Potato flakes, from potatoes obtained from a genetically altered potato plant, comprising poly(3-hydroxybutyrate-co-3-hydroxyheptanoate) are washed with water and then hydrated at 65° C. for 30 min to produce a suspension containing 7% solids by weight. The suspension is then passed through a colloid mill (Littleford, Day, Florence, Ky.]) once to assure complete mixing. The suspension is then passed twice through a homogenizer (Model 3M, Gaulin, Wilmington, Mass.) operated at 8,000 psi to produce a suspension mixture consisting of fine granules of poly(3-hydroxybutyrate-co-3-hydroxyheptanoate) having an average particle size of less than 1μ and other potato biomass debris. The homogenized suspension of potato is fed to a continuous centrifuge (6" Solid Bowl Centrifuge, Bird Machine Co., South Walpole, Mass.) at a feed rate of 1,500 g/min. The supernatant effluent stream coming out of the continuous centrifuge is spray dried to produce a cake of poly(3-hydroxybutyrate-co-3-hydroxyheptanoate) granules with a purity higher than 95%, and a yield of about 85% with respect to the starting material.

EXAMPLE 6

Isolation of Poly(3-hydroxybutyrate) from *A. eutrophus*

A culture of *A. eutrophus* which naturally produces poly (3-hydroxybutyrate) is treated with an ultrasonic sonicator (Branson Ultrasonics Corp., Danbury, Conn.) to produce a suspension mixture consisting of fine granules of poly(3-hydroxybutyrate) having an average particle size of less than 1μ and other bacterial biomass debris containing about 20% solids by weight. The homogenized suspension of bacterial components is fed to a hydrocyclone (Doxie type-A, Dorr-Oliver, Milford, Conn.) with a heavy duty pump pressure of 4 MPa. The effluent stream coming out the top section of the hydrocyclone contains most of the poly(3-hydroxybutyrate) granules. This portion of the suspension is spray dried to produce a cake of poly(3-hydroxybutyrate) granules with a purity higher than 95%, and a yield of about 90% with respect to the starting material.

EXAMPLE 7

Isolation of Poly(3-hydroxybutyrate) from *E. Coli*

A culture of *E. coli* which has been genetically manipulated to produce poly(3-hydroxybutyrate) is treated with an ultrasonic sonicator (Branson Ultrasonics Corp., Danbury, Conn.) to produce a suspension mixture consisting of fine granules of poly(3-hydroxybutyrate) having an average particle size of less than 1μ an other bacterial biomass debris containing about 5% solids by weight. The homogenized suspension of bacterial components is fed to a hydrocyclone (Doxie type-A, Dorr-Oliver, Milford, Conn.) with a heavy duty pump pressure of 4 MPa. The effluent stream coming out the top section of the hydrocyclone contains most of the poly(3-hydroxybutyrate) granules. This portion of the suspension is spray dried to produce a cake of poly(3-hydroxybutyrate) granules with a purity higher than 95%, and a yield of about 90% with respect to the starting material.

All publications and patent applications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. A process for recovering polyhydroxyalkanoate from a biological source material containing the polyhydroxyalkanoate, the process comprising:
   (a) comminuting the biological source material;
   (b) suspending the comminuted biological source material in a suspending fluid having a substantially uniform density wherein the density of said suspending fluid is not intermediate between the polyhydroxyalkanoate and the other components of the biological source material;
   (c) partitioning the polyhydroxyalkanoate from the other components of the biological source material by centrifugal fractionation to form a solid-solid separation, said solid-solid separation being rate driven by both particle size and density; and
   (d) recovering the polyhydroxyalkanoate.

2. The process of claim 1, wherein the biological source material is plant material.

3. The process of claim 2, wherein the centrifugal fractionation is carried out by a hydrocyclone.

4. The process of claim 2, wherein the centrifugal fractionation is carried out by centrifugation.

5. The process of claim 2, wherein the biological source material is avocado, barley, beets, broad bean, buckwheat, carrot, coconut, copra, corn, cottonseed, gourd, lentils, lima bean, millet, mung bean, oat, oilpalm, peas, peanut, potato, pumpkin, rapeseed, rice, sorghum, soybean, sugarbeet, sugar cane, sunflower, sweetpotato, tobacco, wheat, yam, apple, apricot, banana, cantaloupe, cherries, grapes, kumquat, lemon, lime, orange, papaya, peaches, pear, pineapple, tangerines, tomato, or watermelon.

6. The process of claim 5, wherein the biological source material is soybean.

7. The process of claim 5, wherein the biological source material is corn.

8. The process of claim 5, wherein the biological source material is potato.

9. The process of claim 1, wherein the biological source material is bacteria.

10. The process of claim 9, wherein the centrifugal fractionation is carried out by a hydrocyclone.

11. The process of claim 9, wherein the centrifugal fractionation is carried out by centrifugation.

* * * * *